United States Patent
Cai et al.

(10) Patent No.: US 9,609,883 B2
(45) Date of Patent: Apr. 4, 2017

(54) METHOD FOR PRODUCING WHEAT GLUTAMINE PEPTIDE

(71) Applicant: CHINA NATIONAL RESEARCH INSTITUTE OF FOOD AND FERMENTATION INDUSTRIES, Beijing (CN)

(72) Inventors: Muyi Cai, Beijing (CN); Ruizeng Gu, Beijing (CN); Jun Lu, Beijing (CN); Feng Lin, Beijing (CN); Yong Ma, Beijing (CN); Zhe Dong, Beijing (CN); Xingchang Pan, Beijing (CN); Yongqing Ma, Beijing (CN); Yaguang Xu, Beijing (CN); Zhentao Jin, Beijing (CN); Liang Chen, Beijing (CN); Wenying Liu, Beijing (CN); Ying Wei, Beijing (CN); Haixin Zhang, Beijing (CN); Lu Lu, Beijing (CN); Yan Liu, Beijing (CN); Tao Ma, Beijing (CN); Simeng Jiang, Beijing (CN); Kelu Cao, Beijing (CN); Jing Wang, Beijing (CN)

(73) Assignee: CHINA NATIONAL RESEARCH INSTITUTE OF FOOD AND FERMENTATION INDUSTRIES, Beijing (CN)

(*) Notice: Subject to any disclaimer, the term of this patent is extended or adjusted under 35 U.S.C. 154(b) by 0 days.

(21) Appl. No.: 14/515,457

(22) Filed: Oct. 15, 2014

(65) Prior Publication Data
US 2015/0037492 A1 Feb. 5, 2015

Related U.S. Application Data

(63) Continuation of application No. PCT/CN2012/000551, filed on Apr. 24, 2012.

(30) Foreign Application Priority Data

Dec. 23, 2011 (CN) .......................... 2011 1 0439352

(51) Int. Cl.
*C12P 1/00* (2006.01)
*A23J 3/34* (2006.01)
(Continued)

(52) U.S. Cl.
CPC ................. *A23J 3/346* (2013.01); *A23J 3/18* (2013.01); *A23L 33/18* (2016.08); *C07K 4/10* (2013.01);
(Continued)

(58) Field of Classification Search
None
See application file for complete search history.

(56) References Cited

U.S. PATENT DOCUMENTS

2005/0287267 A1* 12/2005 Maningat .................. A23J 1/12 426/549
2010/0105872 A1* 4/2010 De Sadelleer ............ A23J 3/18 530/375

FOREIGN PATENT DOCUMENTS

CN 1570127 * 1/2005
CN 1570127 A 1/2005
(Continued)

OTHER PUBLICATIONS

Kong et al., Food Chem. 102: 759-763 (2007).*
(Continued)

*Primary Examiner* — Erin M Bowers
(74) *Attorney, Agent, or Firm* — J.C. Patents

(57) ABSTRACT

The present invention discloses a method for producing wheat glutamine peptide using wheat gluten powder as raw material, belonging to the fields of food and biotechnology.

(Continued)

The method includes the steps of: performing enzymolysis in two steps using Alcalase and papain with the wheat gluten powder as raw material, to obtain the wheat glutamine peptide with components with molecular weight of less than 1000 Da being more than 90%, characteristic glutamine peptide segment glutamine-arginine-glutamine (Gln-Arg-Gln, QRQ) content being more than 2.0% and glutamine content being up to 23.54% by treating the enzymatic hydrolysate by centrifugation, ultrafiltration, concentration, spray drying, etc. The produced glutamine peptide can be used as functional nutrition composition ingredient in the development and production of ordinary foods, health foods and medicines.

4 Claims, 4 Drawing Sheets

(51) Int. Cl.
    *A23J 3/18*     (2006.01)
    *C12P 21/06*     (2006.01)
    *C07K 5/093*     (2006.01)
    *C07K 4/10*     (2006.01)
    *A23L 33/18*     (2016.01)
    *A61K 38/00*     (2006.01)

(52) U.S. Cl.
    CPC ............ *C07K 5/0819* (2013.01); *C12P 21/06* (2013.01); *A61K 38/00* (2013.01)

(56) References Cited

FOREIGN PATENT DOCUMENTS

| CN | 101627793 | * | 1/2010 |
|---|---|---|---|
| CN | 101627793 A | | 1/2010 |
| CN | 102363799 A | | 2/2012 |

OTHER PUBLICATIONS

Marlene Tsao et al., "Quantification of Glutamine in Proteins and Peptides Using Enzymatic Hydrolysis and Reverse-Phase High-Performance Liquid Chromatography" Analytical Biochemistry, vol. 269, Dec. 1999, pp. 143-148.

Rui-Chang Zhang, "Study on Preparation of Polypeptides by Enzynolysis Wheat Protein and Functional Character" Chinese Master Thesis Paper of Northwest A & F University, Jun. 2006, the whole document.

Xiang-Zhen Kong et al., "Study on Enzymatic Hydrolysis of Wheat Gluten" Cereals & Oils, No. 4, Apr. 2006, pp. 21-23.

Yan LV, "Study on the Active Glutamine Peptides Made from Wheat Protein by Enzymatic Hydrolysis" Chinese Master Thesis Paper of Zhejiang University, May 2005, the whole document.

International Search Report of corresponding International PCT Application No. PCT/CN2012/000551, dated Sep. 27, 2012.

* cited by examiner

METHOD FOR PRODUCING WHEAT GLUTAMINE PEPTIDE

CROSS-REFERENCE TO RELATED APPLICATIONS

This application is a continuation of International Application No. PCT/CN2012/000551, filed on Apr. 24, 2012, which claims the priority to China Patent Application No. 201110439352.3, filed on Dec. 23, 2011, entitled "Method for Producing Wheat Glutamine Peptide". The contents of the above identified applications are hereby incorporated herein by reference in their entireties.

FIELD OF THE TECHNOLOGY

The present invention relates to a method for producing wheat glutamine peptide using wheat gluten powder as raw material, with the product produced therefrom can be used in ordinary foods, health foods and medicines. The present invention belongs to the field of biotechnology.

BACKGROUND

Wheat is a general term for triticum, which is the most widely distributed food crop with the largest consumption population in the world, known as "worldwide food". Gluten powder, also known as vital wheat gluten, refers to the remaining unmodified gluten powder after washing away starch and other water-soluble substances with wheat flour as raw material, and it is a nutritious plant protein source. In the protein composition of the wheat, gluten powder contains about 70% to 80% of protein as the main component, and also contains a small amount of starches, fibers, sugars, fats, lipids, minerals, etc. Wherein, gliadin accounts for 40% to 50%, glutenin for 30% to 40%, globulin for 6% to 10%, and albumin for 3% to 5%, of the total protein.

In the amino acid composition of the wheat, based on total amount of amino acids of wheat protein, there are about 35% of total glutamic acid Glx (Gln+Glu), about 16% of proline, and smaller amount of basic amino acid. Glutamine is the most abundant free amino acids in animal plasma and tissues, which accounts for about 40% to 60% of the total free amino acids. Glutamine is a very important essential amino acid and intestinal essential amino acid with specific nutritional effect. Since Gln has the characteristics of low solubility in water, being unstable in aqueous solution, and acid-sensitive, etc., nutritional and physiological functions of Gln in enteral, parenteral or oral nutrition cannot be fully realized. The peptide obtained by the hydrolysis of protein has better nutrition than the protein, and experiments have confirmed that the peptide has higher absorptivity than amino acid, and is easier and faster to be absorbed and utilized by human body through small intestine membrane.

With the rapid development of science and technology, people have had more deep knowledge to composition and functional properties of protein of gluten powder, which has greatly broadened its application fields. In recent years, due to the constant increase in the production of gluten powder, the traditional market is becoming saturated. So it is very urgent and necessary to develop an industrial method for deep and fine processing of the gluten powder to explore high value-added foodstuffs for maximizing gluten powder nutrition.

Enzymolysis of wheat gluten powder by protease may enzymolyze the whole protein into oligopeptides with smaller molecular weight and greatly increase the solubility of the product and release the glutamine therein, which facilitates preparation of glutamine-rich wheat glutamine peptide. The successful preparation of wheat glutamine peptide provides a new industrial way for deep processing wheat gluten powder agricultural products as traditional food, so that the abundant ordinary food protein resources-wheat gluten powder are fully utilized, which greatly expands the application fields of the wheat gluten powder as a raw material for the traditional ordinary food, and improves the added value of bulk agricultural products, thus realizing greater economic value and improving the overall social benefits.

Compared with the original protein, wheat glutamine peptide with small molecule has good processability. For example, wheat glutamine peptide is more stable under acidic conditions, not easy to precipitate; and it will not heat coagulated when heated and has no protein denaturation problems. The wheat glutamine peptide has good water-solubility due to its small molecular weight and large polarity. Wheat glutamine peptide, as a food raw material, is characterized by high concentration, low viscosity, rapid soluble in water, no residue, etc., and will maintain good flowability even at high concentration of 50%. Wheat glutamine peptide has strong hygroscopicity and moisture retention, which can inhibit the protein from forming a gel and, thus, adjust the hardness of protein food.

Due to a series of excellent food processabilities, wheat glutamine peptide can be mixed with proteins from various sources, to improve their nutritional value, and also can be used to produce instant drinks, functional drinks, meat products, milk products, baked goods and other diverse food. In addition, wheat glutamine peptide can be used as a protein supplement in diet for the elderly, sports nutrition, weight controlling, etc., or as a nutritional component of foods provided for patients with digestion and absorption dysfunctions and also as baby food, and also can be added into the emerging wine beverage products.

Wheat glutamine peptide, due to its high safety, nutritional value and good processability, can be added into many food products, and thus has a good market prospect.

SUMMARY

The object of the present invention is to broaden the approach for wheat gluten powder processing and utilization and overcome the current shortcomings of unclear activity, indefinite characteristic peptide segment, small production scale, etc. of the wheat peptide, so as to develop an industrial method for obtaining wheat glutamine peptide from wheat gluten powder.

To achieve the above object, a method which combines alkali-heat treatment and continuous enzymatic hydrolysis is used in the present invention, where the wheat gluten powder is mixed with water with a liquid-feed ratio of 100:6-12 (L:kg) to form a slurry in a reaction tank, the slurry is adjusted to pH 8-12 such as 9-11, heated to 50-90° C. such as 60-80° C. and kept at this temperature for 20-90 min such as 40-60 min while stirring, to form a basic liquid material. The basic liquid material in the reaction tank is then pumped into a chip centrifuge, to be separated into supernatant and residue. The residue is collected and used as raw material to be further processed by diluting, heating, stirring and separating under the same conditions as mentioned above, this process is repeated for three times to obtain purified residue. The purified residue is mixed with water with a water-residue ratio of 100:40-50, stirred, adjusted to pH 7-9, and heated to 40-60° C. ALCALASE (subtilisin A from *Bacillus*

*licheniformis*) is then added thereto in an amount of 1000-8000 such as 2000-5000 units per gram protein in the wheat gluten powder, to react for 3 to 5 hours. After that, papain is added thereto in an amount of 1000-2000 such as 1300-1700 units per gram protein in the wheat gluten powder, to perform enzymatic hydrolysis under a temperature of 45-55° C. for 1 to 2 hours, to obtain enzymatic hydrolysate. Finally, the enzymatic hydrolysate is heated to 120-135° C. such as 125-130° C. and kept at this temperature for a period of time to conduct enzyme inactivation, to obtain a wheat protein enzymatic hydrolysate. The time period for keeping the enzymatic hydrolysate at the temperature of 120-135° C. is not particularly limited as long as the enzyme can be inactivated, for example the time period can be 5 s to 10 min or 15 min, for a fast enzyme inactivation, the time period can be 15-25 s.

The wheat protein enzymatic hydrolysate is centrifuged with a tubular centrifuge at a speed of 9000-16000 r/min such as 12000-14000 r/min, the centrifugal clear liquid is collected and filtered by a microfiltration equipment and an ultrafiltration equipment with a pore size of 0.05-0.1 µm under a pressure of 0.2-0.4 MPa and a temperature of 30-80° C., to obtain a permeate liquid of wheat glutamine peptide. The permeate liquid of wheat glutamine peptide is concentrated by a double-effect falling-film evaporator under a vapor pressure of 0.1±0.02 MPa and a temperature of 40-80° C., until the concentrated liquid has 20-50% of solid content. The concentrated liquid is heated to 70-95° C. such as 80-90° C. under stirring, active carbon is added in the amount 5-10% such as 6-8% of the solid content after the concentrated liquid is heated to 70-95° C., and stirred at this temperature for 20-40 min to decolorize the concentrated liquid. The decolorized concentrated liquid is then filtered with frame filter to obtain a concentrated liquid of wheat glutamine peptide. After that, the concentrated liquid of wheat glutamine peptide is dried by a centrifugal spray drier under an inlet temperature of 160-180° C. and an outlet temperature of 80-90° C., to finally obtain the wheat glutamine peptide powder.

The basic physical and chemical components of the wheat glutamine peptide prepared are determined by chemical component analysis, and the molecular weight distribution of the wheat glutamine peptide component is determined by high-performance liquid chromatography. It has been found that the component with molecular weight of less than 1000 Da account for more than 90% Amino acid analysis and liquid chromatography analysis show that total glutamic acid content in the wheat glutamine peptide is 34.6%, wherein the content of glutamine is up to 23.54%. After separation and structural identification of the peptide segments in the wheat glutamine peptide by LC-MS analysis, it has been determined that content of the characteristic peptide segment, glutamine-arginine-glutamine (Gln-Arg-Gln, QRQ), is above 2.0%.

Wheat glutamine peptide produced by this method can be used in health food and medicine fields.

BRIEF DESCRIPTION OF THE DRAWINGS

The following is a brief description of the drawings.

DETAILED DESCRIPTION

Figure 1:
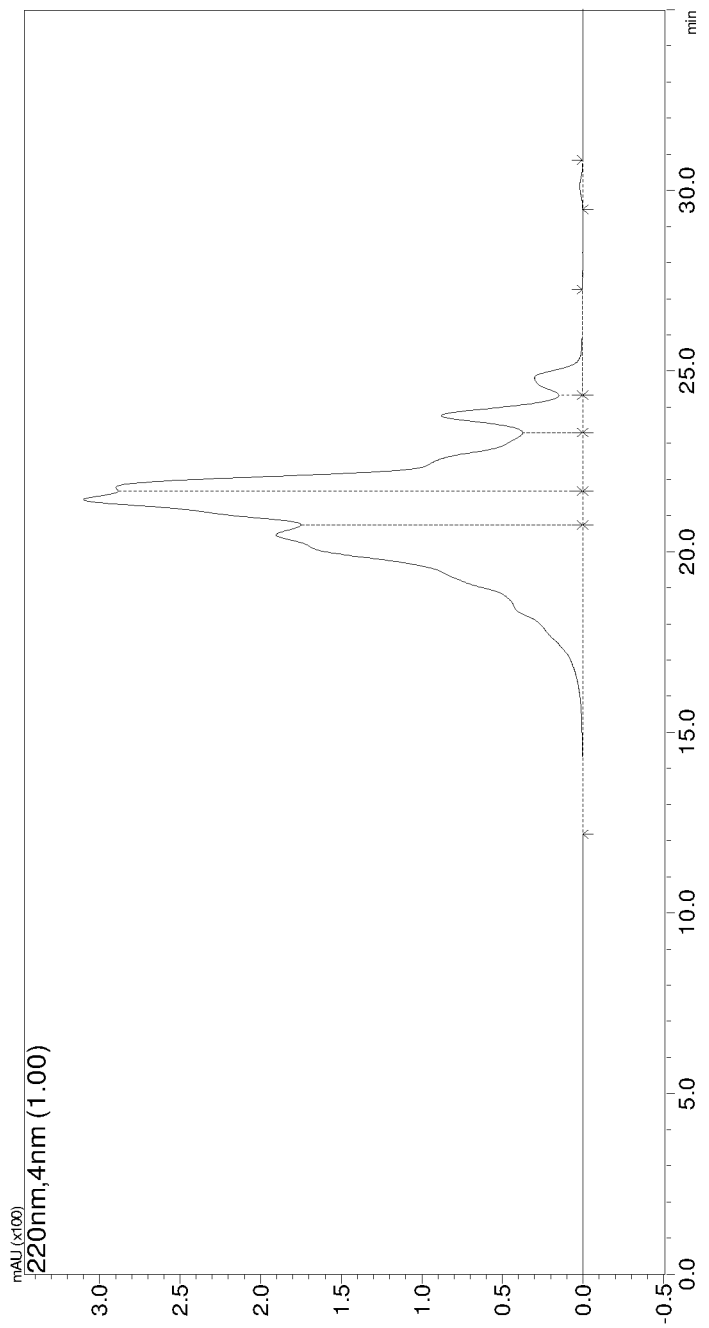
FIG. 1 is a molecule gel HPLC chromatogram (220 nm) of wheat glutamine peptide.

The present invention will be described in further detail below with reference to the drawings and specific embodiments, but the scope of the invention is not limited thereto. The specific process includes the following steps:

1. Preparation of Wheat Glutamine Peptide 500 kg of wheat gluten powder were added into a reaction tank I and mixed with water with a liquid-feed ratio of 100:9(L: kg) to form a slurry. The slurry is adjusted to pH 10, heated to 65° C. and kept at this temperature for 40 min under stirring, to obtain a basic liquid material. The basic liquid material was pumped into a chip centrifuge to be separated into supernatant and residue. The residue was collected and added into a reaction tank II, and the supernatant was discarded. The residue was used as raw material to be further processed by diluting, heating, stirring and separating under the same conditions as mentioned above. This process is repeated for three times to remove oil, starch, fiber and other non-protein substances, so as to obtain a purified residue. The purified residue was mixed with water with a water-residue ratio of 100:45 and stirred. The resulting wheat protein solution was then adjusted to pH 8, and heated to 50° C., and ALCALASE (subtilisin A from *Bacillus licheniformis*) was then added thereto in an amount of 3500 units per gram protein in the wheat gluten powder, to react for 4 hours under this condition. Then, papain was added thereto in an amount of 1500 units per gram protein in the wheat gluten powder under the temperature of 50° C., to conduct enzymatic hydrolysis for 1.5 hours, to obtain enzymatic hydrolysate. The enzymatic hydrolysate was then heated to 120° C., and kept at this temperature for 20 s to inactivate the enzyme, to obtain wheat protein enzymatic hydrolysate.

The wheat protein enzymatic hydrolysate was centrifuged with a tubular centrifuge at a speed of 14000 r/min and separated into centrifugal clear liquid and residue. The centrifugal clear liquid was filtered by a microfiltration equipment and an ultrafiltration equipment with a pore size of 0.06 µm under a pressure of 0.3 MPa and a temperature of 55° C., to obtain a clear permeate liquid of wheat glutamine peptide. The permeate liquid was concentrated by a double-effect falling-film evaporator under a vapor pressure of 0.1 MPa and a temperature of 60° C., until the concentrated liquid had 40% of solid content. The concentrated liquid was heated to 80° C. under stirring and active carbon was added in the amount of 5% of the total solid content in the concentrated liquid, kept at this temperature and continue to stir for 30min, and then filtered. After that, the wheat glutamine peptide concentrated liquid was dried by a centrifugal spray drier under an inlet temperature of 170° C. and an outlet temperature of 85° C., to finally obtain 205.32 kg of wheat glutamine peptide.

2. Analysis of Physical and Chemical Components and Molecular Weight Distribution of the Wheat Glutamine Peptide Analysis results on components of the wheat glutamine peptide are shown in table 1. It can be seen that the wheat glutamine peptide prepared according to the present invention includes as high as 98.3% of total protein content, i.e., the wheat glutamine peptide has very high quality.

The wheat glutamine peptide sample was injected into GEL-HPLC, to obtain a gel chromatogram, as shown in FIG. 1. Gel chromatography data of the wheat glutamine peptide was substituted into a calibration curve equation using a data processing software for liquid phase chromatography, to calculate relative molecular mass and its distribution of the peptide in the sample. In components with molecular weight of below 1000 Da, dipeptide and tripeptide may be absorbed and utilized in the human body in a very high ratio, and thus have higher nutritional value and physiological functions than free amino acids. The relative molecular mass distribution of the wheat glutamine peptide was calculated by the peak area normalization method, as shown in table 2. It can be seen from the results of molecular mass distribution, the components with the molecular weight of less than 1000 Da was 92.32% of the total components. Assuming that the average molecular weight of the amino acids is 137 Da, it can be calculated that the components with the molecular weight of below 1000 Da mainly is oligopeptides that has less than eight peptides, also including some free amino acids. The components with the molecular weight of 140 Da-500 Da were 61.31%, accounting for most of the components with molecular weight of below 1000 Da, which mainly were dipeptide, tripeptide and tetrapeptide.

TABLE 1

Basic physical and chemical component of the wheat glutamine peptide

| Component | Content/% |
| --- | --- |
| Total protein (dry) | 98.3 ± 0.56 |
| Fat | 0.05 ± 0.01 |
| ash | 4.56 ± 0.25 |

TABLE 2

The molecular weight distribution of the wheat glutamine peptide

| Molecular weight range | Start time (min) | End time (min) | Weight average molecular weight | Peak area percentage (%, λ220 nm) |
| --- | --- | --- | --- | --- |
| Above 10000 | 8.892 | 13.920 | 14112 | 0.0096 |
| 3000-10000 | 13.920 | 16.549 | 4186 | 0.3435 |
| 1000-3000 | 16.549 | 18.948 | 1473 | 7.2012 |
| 500-1000 | 18.948 | 20.461 | 673 | 22.7846 |
| 140-500 | 20.461 | 23.241 | 314 | 60.3163 |
| Below 140 | 23.241 | 28.795 | 101 | 9.2174 |
| Weight average molecular weight | | | | 473.85 |
| Percentage of hydrolysate with relative molecular mass of less than 1000 (%) | | | | 92.32 |

3. Glutamine Content of Wheat Glutamine Peptide Powder

Since protein content in wheat glutamine peptide powder is very high, which can be above 98%, the main component of the wheat glutamine peptide powder is protein. Composition of the amino acids in the wheat glutamine peptide powder were analysed. First, the glutamine peptide were hydrolyzed into free amino acids by hydrochloride (glutamine was converted into glutamic acid under the acidic condition), and then the content of total glutamic acid Glx (Gln+Glu) was detected by an amino acid analyzer. The results showed that the total glutamic acid in the wheat glutamine peptide powder was up to 34.60%.

Using a BTI-AQC two-step precolumn derivatization to further detect the effective content of the glutamine peptide, it was found that the content of Gln in the wheat glutamine peptide (non-free glutamine) was 23.54%, much higher than that in other common edible protein peptide products.

Among most of the edible proteins, wheat protein has the most abundant total glutamic acid. The wheat glutamine peptide powder is rich in glutamine. Under normal physiological conditions, the intestine neither synthesizes nor stores glutamine, and a large number of glutamine required for intestinal cell proliferation derives from in vivo synthesis. Glutamine is the major energy source for intestinal epithelial cells, and also an important component for synthesis of nucleic acids. Therefore glutamine is a particular amino acid that is essential to keep structural integrity of intestinal mucosa.

TABLE 3

Composition of amino acids in wheat glutamine peptide powder

| Ammo acid | Content (g/100 g) |
| --- | --- |
| Total glutamic acid (Gln + Glu) | 34.60 |
| Threonine, Thr | 2.60 |
| Serine, Ser | 4.50 |
| Aspartic acid, Asp | 2.45 |
| Glycine, Gly | 4.27 |
| Alanine, Ala | 1.97 |
| Valine, Val | 4.15 |
| Methionine, Met | 2.60 |
| Isoleucine, Ile | 1.85 |
| Leucine, Leu | 5.06 |
| Tyrosine, Tyr | 0.85 |
| Phenylalanine, Phe | 3.63 |
| Lysine, Lys | 0.93 |
| Histidine, His | 2.81 |
| Arginine, Arg | 1.34 |
| Proline, Pro | 10.10 |
| Cysteine, Cys | 0.84 |
| Tryptophane, Trp | 6.30 |
| Total content | 90.85 |

4. Structure Identification of the Wheat Glutamine Peptide and Quantitation of Characteristic Glutamine Peptide Segment The latest nutrition research at home and abroad has shown that protein ingested is not completely hydrolyzed into amino acids, but most are digested and absorbed by the body in the form of peptides. Beside nutrition functions of easy digesting and absorbing, the more important biological significance of the peptides is mainly reflected in the physiological activity which is unparalleled by amino acids. As a hybrid peptide, the wheat glutamine peptide contains many peptides having different physiological functions. Meanwhile, in the wheat glutamine peptide, the components with the relative molecular mass of less than 1000 is above 90%, indicating that the product is essentially composed of short peptides. The specific source of protein and the unique production process results in that the wheat glutamine peptide product contains a certain amount of characteristic peptides.

We conducted separation and structural identification to the peptide segment of the wheat glutamine peptide. The peptide segment separation and structural identification were performed by high performance liquid chromatography and mass spectrometry analysis. Primary structures of 40 peptide segments were identified in total.

Figure 2:
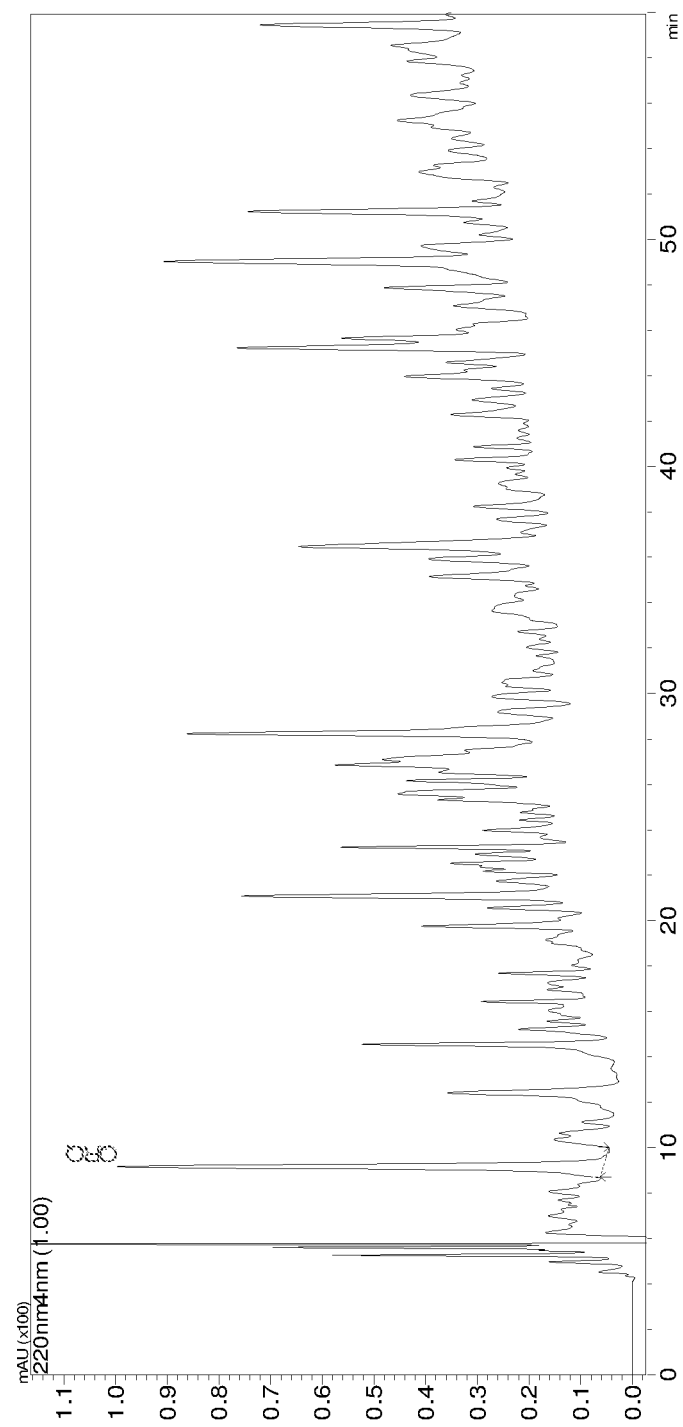
FIG. 2 is a QRQ (Gln-Arg-Gln: RT=9.17 min) chromatographic peak in wheat glutamine peptide reversed phase chromatogram.
Figure 3:
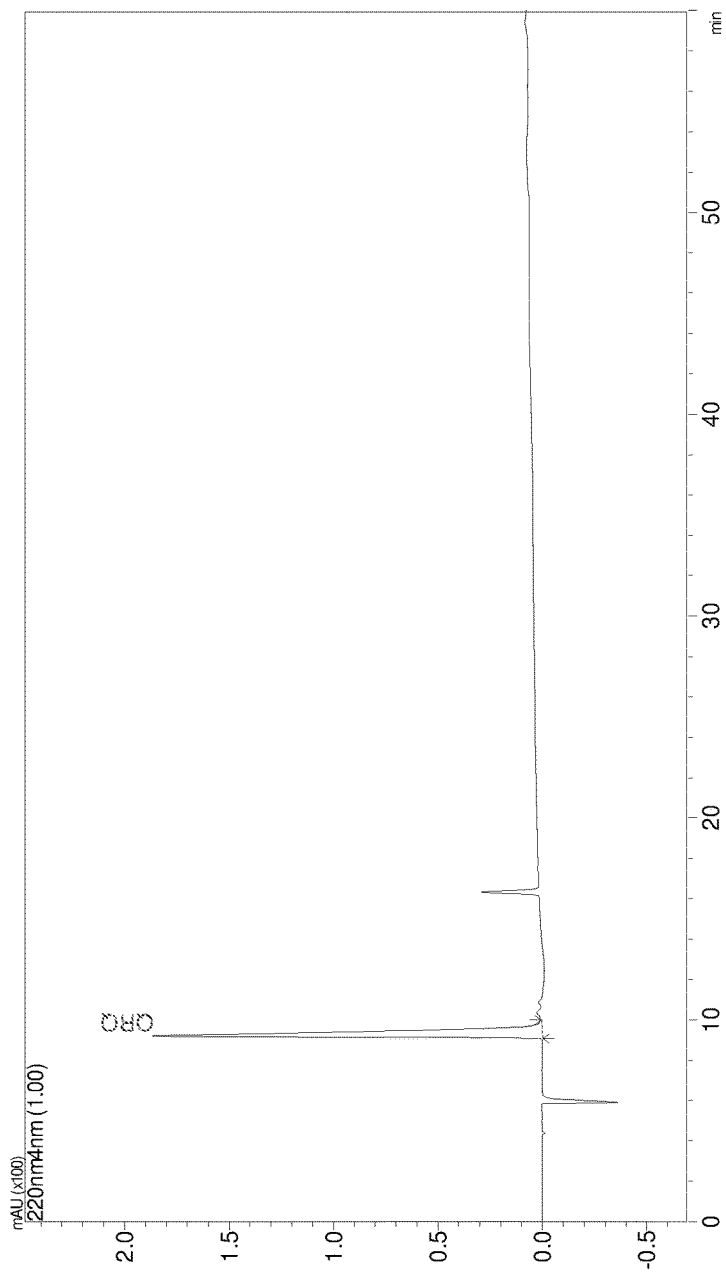
FIG. 3 is a HPLC chromatogram of the QRQ standard (Gln-Arg-Gln: RT=9.17 min).
Figure 4:
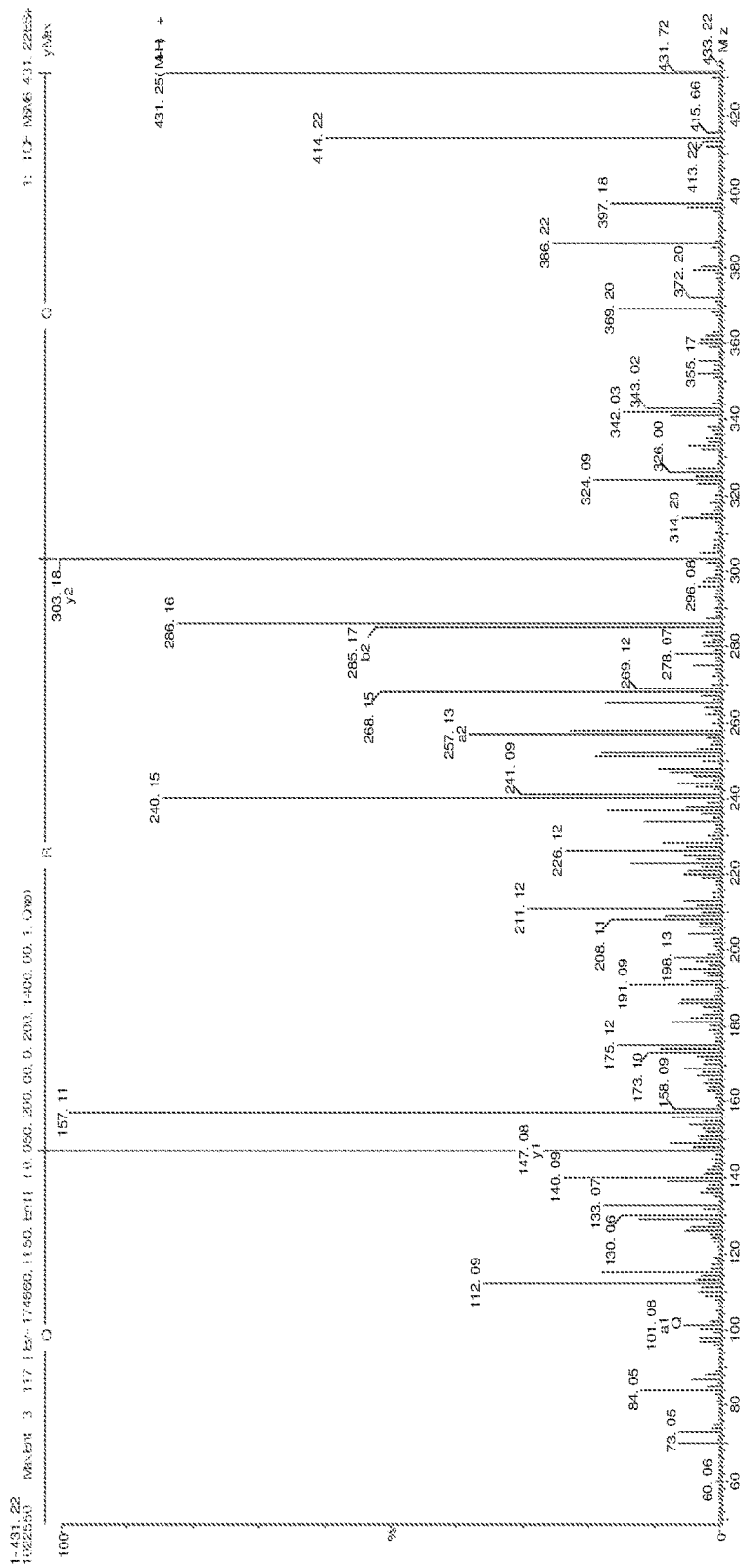
FIG. 4 is a tandem mass spectrum of QRQ (Gln-Arg-Gln) in wheat glutamine peptide.

We have developed a HPLC analysis method for quantitative determination of QRQ (Gln-Arg-Gln) in wheat glutamine peptide. In this method, the wheat glutamine peptide sample was pre-treated, and then separation was conducted reversed based on the difference between the polarities of the molecules in the sample with the reversed phase C18 packing as stationary phase. The separated components were detected by UV absorption at 220 nm wavelength, quantified using an external standard method, and the resulting chromatogram and its data were processed (FIG. 2, and FIG. 3) to calculate the content of QRQ. Since different batches of the wheat glutamine peptide samples all contained QRQ in the amount of above 2.0%, QRQ was selected to be the characteristic component of the wheat glutamine peptide. A tandem mass spectrum of QRQ is shown in FIG. 4.

What is claimed is:

1. An industrial enzymatic hydrolysis method for producing glutamine peptide from wheat gluten powder, comprising the following steps:
   1) mixing the wheat gluten powder with water with a liquid-feed ratio of 100:2-20 (L:kg) to form a slurry, adjusting the slurry to pH 8-12, heating to 50-90° C. and stirring at this temperature for 20-90 min, to form a basic liquid material,
   2) separating the basic liquid material into supernatant and residue, collecting the residue and diluting the residue with water, heating to 50-80° C., stirring and separating, to obtain a purified residue, and
   3) mixing the purified residue with water with a water-residue ratio of 100:10-50, stirring, adjusting to pH 7-9, heating to 40-60° C., and then adding subtilisin A from *Bacillus licheniformis* in an amount of 1000-8000 units per gram protein, reacting for 1-5 h to obtain a first enzymatic hydrolysate, after that, without removing or inactivating the subtilisin A in the first enzymatic hydrolysate, directly adding papain in an amount of 1000-2000 units per gram protein to the first enzymatic hydrolysate, and performing enzymatic hydrolysis under a temperature of 45-55° C. for 1-3 h, to obtain a second enzymatic hydrolysate, heating the second enzymatic hydrolysate to 120-135° C. to conduct enzyme inactivation, to obtain wheat protein enzymatic hydrolysate;

wherein after step 3), the method further comprising:
   4) centrifuging the wheat protein enzymatic hydrolysate with a tubular centrifuge, collecting centrifugal clear liquid, filtering the centrifugal clear liquid by a microfiltration equipment and an ultrafiltration equipment with a pore size of 0.05-0.1 μm under a pressure of 0.2-0.4 MPa and a temperature of 30-80° C., to obtain a clear permeate liquid of wheat glutamine peptide,
   5) evaporating the clear permeate liquid by a double-effect falling-film evaporator under vapor pressure of 0.1±0.02 MPa and a temperature of 40-80° C., until the solid content of the clear permeate liquid reaches to 20-50%; and then heating to 70-95° C., adding active carbon in the amount of 5-10% of the solid content, and stirring at this temperature for 20-40 min to perform decolorization, so as to obtain a concentrated liquid of wheat glutamine peptide,
   6) drying, by a centrifugal spray drier, the concentrated liquid of wheat glutamine peptide under an inlet temperature of 160-180° C. and an outlet temperature of 80-90° C., to obtain wheat glutamine peptide powder.

2. The method according to claim 1, wherein in step 3), time for enzyme inactivation is 15-25 s.

3. The method according to claim 1, wherein the speed of the tubular centrifuge is 9000-16000 r/min.

4. The method according to claim 1, wherein, in the wheat protein enzymatic hydrolysate, peptides with molecular weight of less than 1000 Da is above 90% and contents of free amino acids is below 5%.

* * * * *